United States Patent [19]

Bradshaw

[11] 4,440,938
[45] Apr. 3, 1984

[54] PROCESS FOR THE PREPARATION OF A FURAN DERIVATIVE

[75] Inventor: John Bradshaw, Hertfordshire, England

[73] Assignee: Glaxo Group Limited, London, England

[21] Appl. No.: 431,600

[22] Filed: Sep. 30, 1982

Related U.S. Application Data

[63] Continuation of Ser. No. 223,483, Jan. 8, 1981, abandoned.

[30] Foreign Application Priority Data

Jan. 8, 1980 [GB] United Kingdom ................. 8000580
Jan. 8, 1980 [GB] United Kingdom ................. 8000581

[51] Int. Cl.³ .......................................... C07D 307/52
[52] U.S. Cl. ................................................... 549/495
[58] Field of Search ........................................ 549/495

[56] References Cited

U.S. PATENT DOCUMENTS 4,276,421  6/1981  Baudet ................................ 548/342

FOREIGN PATENT DOCUMENTS

WO79/00466  7/1979  PCT Int'l Appl. .
2036003  6/1980  United Kingdom .

Primary Examiner—Richard Raymond
Attorney, Agent, or Firm—Bacon & Thomas

[57] ABSTRACT

The invention relates to a process for the preparation of ranitidine of formula (I)

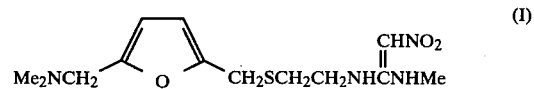

which comprises reacting a thiol of formula (II)

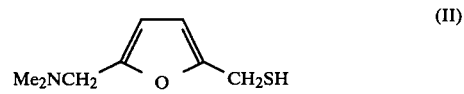

with an alkylating agent of formula (III)

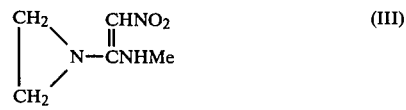

The ethyleneimino derivative of formula (III) is a novel compound.

5 Claims, No Drawings

PROCESS FOR THE PREPARATION OF A FURAN DERIVATIVE

This application is a continuation of application Ser. No. 223,483, filed Jan. 8, 1981, now abandoned.

This invention relates to a process for the preparation of a furan derivative.

The furan derivative of formula (I)

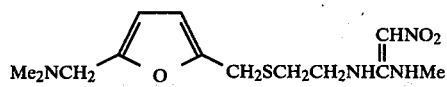

which is known as ranitidine is disclosed in British Patent Specification No. 1,565,966 as a potent and selective $H_2$—antagonist.

The present invention provides a process for the preparation of the furan derivative of formula (I) which comprises reacting a thiol of formula (II)

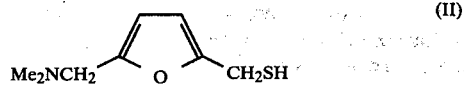

with an alkylating agent of formula (III)

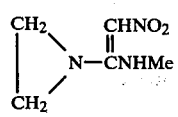

The process of the present invention provides a novel and useful method for the preparation of the compound ranitidine.

The reaction may be carried out in the absence or presence of a solvent. Suitable solvents include water, an alkanol (e.g. methanol) or dimethylformamide. The reaction is preferably carried out with heating, for example at 100° C., and in an inert atmosphere, for example under nitrogen.

The thiol (II) may be used directly or generated in situ from an acid addition salt such as an oxalate salt.

The thiol of formula (II) may be prepared by reacting the corresponding alcohol of formula (IV)

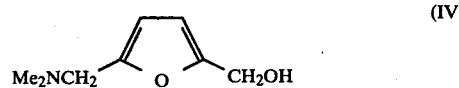

with thiourea in the presence of a concentrated acid such as concentrated hydrochloric acid to produce the isothiourea (V)

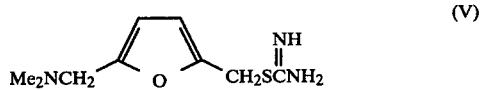

which is then converted into the thiol of formula (II) by treatment with a base such as sodium carbonate or 5 N sodium hydroxide, preferably in the presence of an anti-oxidant such as sodium dithionite or sodium metabisulphite.

Once isolated, the free base thus formed may be converted into a stable acid addition salt by treatment with an appropriate acid, in particular oxalic acid, preferably in a solvent such as tetrahydrofuran.

The compound of formula (III) may be prepared by reaction of ethyleneimine with a nitroethenamine of formula (VI)

where L is a leaving group for example a $C_{1-4}$ alkoxy group or a $C_{1-4}$ alkylthio group, preferably methylthio. The reaction may be carried out in a suitable aprotic solvent such as acetonitrile.

The compound of formula (III) is a novel compound and should be regarded as part of the present invention.

The thiol of formula (II) and the isothiourea of formula (V) are not particularly stable but it has been found that they can be stabilised by converting them into the form of an acid addition salt. Examples of such stable acid addition salts include hydrochlorides, sulphates, alkyl and aryl sulphonates, acetates, fumarates, maleates and benzoates. A preferred acid addition salt of the thiol of formula (II) is an oxalate, and a preferred acid addition salt of the isothiourea (V) is the bis maleate.

The invention is illustrated by the following Examples.

PREPARATION 1

5-[(Dimethylamino)methyl]-2-furanmethanethiol, oxalate (1:1)

5-[(Dimethylamino)methyl]-2-furanmethanol (7.76 g) was added gradually to a solution of thiourea (3.81 g) in concentrated hydrochloric acid (12.5 ml). After 18 h, the solution was heated for 30 minutes at 98°–100° and evaporated to low bulk. A solution of sodium hydroxide (10 g) in water (50 ml) and sodium dithionite (10 g) was added and after 1 h the solution was extracted with ether (6×50 ml). Boric acid (35 g) was added to the aqueous fraction and the suspension was extracted with ether (4×50 ml). To the combined ethereal extracts was added sodium dithionite (2 g) and an excess of anhydrous sodium carbonate. After 3 h, the mixture was filtered into a solution of oxalic acid (6.3 g) in dry tetrahydrofuran (60 ml). The solid which separated was filtered, washed with tetrahydrofuran and dried to give the title compound (5.84 g), m.p. 116.5°–118°.

PREPARATION 2

N-Methyl-α-(nitromethylene)-1-aziridinemethanamine

A solution of ethyleneimine (0.47 g) and N-methyl-(1-methylthio)-2-nitroetheneamine (1.48 g) in acetonitrile (5 ml) was stirred at room temperature for 2 days. The suspension was evaporated in vacuo at room temperature and the residue extracted with hot ethyl acetate (100 ml). Evaporation of the extract in vacuo gave a residue which was suspended in ethyl acetate (50 ml) and filtered. The filtrate was evaporated to ca. 5 ml and chromatographed (silica/ethyl acetate). The appropriate eluate [TLC (silica/ethyl acetate) $R_f$ 0.28] was evaporated in vacuo to give the title compound (0.33 g), m.p. 118°–119°.

EXAMPLE 1

N-[2-[[5-[(Dimethylamino)methyl]-2-furanylmethyl]thio]ethyl]-N'-methyl-2-nitro-1,1-ethenediamine To a mixture of 5-[(dimethylamino)methyl]-2-fuanmethanethiol, oxalate (1:1) (0.156 g), sodium dithionite (0.05 g) and anhydrous sodium carbonate (0.15 g) in water (0.4 ml) was added ether (15 ml) and an excess of anhydrous sodium carbonate. The mixture was filtered and the filtrate evaporated in vacuo. To the residue was added N-methyl-α-(nitromethylene)-1-aziridinemethanamine (0.072 g) and methanol (2 ml) and the solution evaporated to dryness. The residue was heated at 98°–100° for 1.25 h and the product chromatographed (silica/methanol −0.88 ammonia, 79:1). The appropriate eluate was evaporated in vacuo to give the title compound (0.113 g), which had an n.m.r. identical to that of the product prepared according to the method of Example 15 of British Patent Specification No. 1,565,966.

I claim:

1. A process for the preparation of the furan derivative of formula (I)

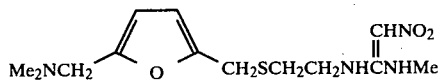
(I)

which comprises reacting a thiol of formula (II)

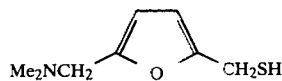
(II)

with an alkylating agent of formula (III)

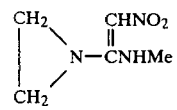
(III)

2. A process according to claim 1 in which said thiol of formula (II) is generated in situ from an acid addition salt.

3. A process according to claim 2 in which the acid addition salt of formula (II) is a hydrochloride, sulphate, alkyl sulphonate, aryl sulphonate, acetate, fumarate, maleate, oxalate or benzoate.

4. A process according to claim 3, wherein the acid addition salt is an oxalate.

5. A process according to claim 1, wherein the thiol of formula (II) is prepared by reacting an alcohol having a formula (IV)

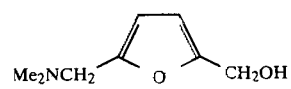
(IV)

with thiourea to produce an isothiourea having the formula (V)

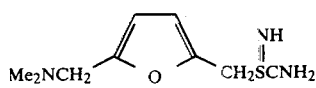
(V)

which is then reacted with a base to produce the thiol of formula (II).

* * * * *